US012727979B2

(12) United States Patent
Huang et al.

(10) Patent No.: US 12,727,979 B2
(45) Date of Patent: Sep. 8, 2026

(54) ANTI-CARIES FILM, ANTI-CARIES SOLUTION, DENTAL APPLIANCE HAVING THE ANTI-CARIES FILM, AND METHOD FOR FORMING ANTI-CARIES FILM ON DENTAL APPLIANCE

(71) Applicant: SHANGHAI EA MEDICAL INSTRUMENTS COMPANY LIMITED, Shanghai (CN)

(72) Inventors: Lei Huang, Shanghai (CN); Shida Lyu, Shanghai (CN)

(73) Assignee: SHANGHAI EA MEDICAL INSTRUMENTS COMPANY LIMITED, Shanghai (CN)

( * ) Notice: Subject to any disclaimer, the term of this patent is extended or adjusted under 35 U.S.C. 154(b) by 635 days.

(21) Appl. No.: 18/044,832

(22) PCT Filed: Jun. 16, 2021

(86) PCT No.: PCT/CN2021/100293
§ 371 (c)(1),
(2) Date: Mar. 10, 2023

(87) PCT Pub. No.: WO2022/052544
PCT Pub. Date: Mar. 17, 2022

(65) Prior Publication Data

US 2023/0285128 A1 Sep. 14, 2023

(30) Foreign Application Priority Data

Sep. 14, 2020 (CN) ......................... 202010958966.1

(51) Int. Cl.
*A61C 17/00* (2006.01)
*A61C 7/08* (2006.01)
*A61C 19/06* (2006.01)
*A61K 6/20* (2020.01)

(52) U.S. Cl.
CPC .............. *A61C 17/005* (2013.01); *A61C 7/08* (2013.01); *A61C 19/063* (2013.01); *A61K 6/20* (2020.01)

(58) Field of Classification Search
CPC ....... A61C 17/005; A61C 7/08; A61C 19/063; A61K 6/20
See application file for complete search history.

(56) References Cited

U.S. PATENT DOCUMENTS

| | | | | |
|---|---|---|---|---|
| 2003/0211440 | A1* | 11/2003 | Kuo ..................... | A61C 19/063 433/215 |
| 2015/0257983 | A1 | 9/2015 | Lendenmann et al. | |
| 2017/0112949 | A1 | 4/2017 | Lahann et al. | |
| 2017/0128346 | A1* | 5/2017 | Dong .................. | A61K 8/8164 |

FOREIGN PATENT DOCUMENTS

| | | | | |
|---|---|---|---|---|
| CA | 1030452 | A * | 5/1978 | |
| CN | 1160540 | A | 10/1997 | |
| CN | 1401376 | A | 3/2003 | |
| CN | 104983610 | A | 10/2015 | |
| CN | 105232165 | A | 1/2016 | |
| CN | 107149506 | A | 9/2017 | |
| CN | 108601851 | A | 9/2018 | |
| GB | 1474486 | A | 5/1977 | |
| JP | 2002114677 | A | 4/2002 | |
| RU | 2245710 | C2 | 2/2005 | |
| WO | WO-2013092117 | A2 * | 6/2013 | ........... A61K 8/9789 |

OTHER PUBLICATIONS

C. Bruun, H. Givskov, and K. Stoltze. "In vivo Uptake and Retention of Fluoride in Human Surface Enamel after Application of a Fluoride-Containing Lacquer (Fluor Protector®)," Caries Res. 14: 103-109 (1980). (Year: 1980).*
SciFinder Search Results_Nov. 14, 2025 (Year: 2025).*
Office Action issued in Chinese Patent Application No. 202010958966.1 dated Jun. 27, 2024, 48 pages, along with English translation.
Search Report issued in Chinese Patent Application No. 202010958966.1 dated Jun. 27, 2024, 4 pages, along with English translation.
Arends, J. et al.. "Fluoride Content in Human Enamel after Fluoride Application and Washing—An in vitro Study." Caries Res., vol. 9, Dec. 31, 1975 (Dec. 31, 1975), pp. 362-372.
Dijkman. A.G. et al.. "In vivo Investigation on the Fluoride Content in and on Human Enamel after Topical Applications." Caries Res., vol. 17, Dec. 31, 1983 (Dec. 31, 1983), pp. 392-402.
Wu. Xueying et al., "Preventive Efficiency and Cost-Effectiveness of Silane Fluoride Garnish on Approximal Caries in Primary Molars", Chinese Journal of Conservative Dentistry, vol. 16, No. 6, Dec. 31, 2006.
Galuscan, A. et al.. "SEM Analysis of Hybrid Layer Adhesion in Substances Used for Dentinal Hypersensitivity." REV.CHIM. (Bucharest)., vol. 67, No. 6, Dec. 31, 2016 (Dec. 31, 2016), pp. 1214-1217.
Sancakli, H. S. et al. . "The influence of varnish and high fluoride on erosion and abrasion in a laboratory investigation." Australian Dental Journal, vol. 60, Dec. 31, 2015.

* cited by examiner

*Primary Examiner* — Michael P Cohen
(74) *Attorney, Agent, or Firm* — MH2 Technology Law Group, LLP

(57) ABSTRACT

In one aspect, the present application provides an anti-caries film, it contains a fluorine-containing silane, a film-forming agent, and an acidic substance.

16 Claims, 2 Drawing Sheets

A-A

ANTI-CARIES FILM, ANTI-CARIES SOLUTION, DENTAL APPLIANCE HAVING THE ANTI-CARIES FILM, AND METHOD FOR FORMING ANTI-CARIES FILM ON DENTAL APPLIANCE

FIELD OF THE APPLICATION

The present application generally relates to anti-caries film, anti-caries solution, dental appliance having anti-caries film and method for forming anti-caries film on dental appliance.

BACKGROUND

Caries is one of common dental diseases. The investigation of the national health organization shows that the dental caries occurrence rate of Chinese children's deciduous teeth reaches 70%, the dental caries occurrence rate of 12-year-old children's permanent teeth is approximately 50%, and the dental caries occurrence rate of adults reaches 88%. Therefore, it is of great importance to prevent caries.

Generally, there are mainly two types of bacteria that cause caries: one is acidogenic bacteria (e.g. *Streptococcus mutans, Actinomyces* and *Lactobacillus*) which enables food residue (e.g. carbohydrate) to decompose to produce acid, thereby causing demineralization of inorganic matter of teeth; the other type of bacteria (e.g. Gram-positive cocci) destroys organic matter, and form carious cavities after long-term action.

Caries can be prevented. At present, fluoride is an internationally recognized effective anti-caries substance. Fluoride is able to inhibit reproduction of cariogenic bacteria in oral cavity and suppress acid production of bacteria, meanwhile reduce solubility of enamel on tooth surface, and promote remineralization of demineralized enamel. Intake of a proper amount of fluoride during teeth development makes cusps smooth and fissures shallow. Such change on geometries of teeth makes it easier to keep teeth clean and enhances resistance to caries.

At present, there are mainly three types of anti-caries techniques using fluoride as follows:

Fluoride toothpaste, which is the most common anti-caries technique at present. An inorganic fluoride such as sodium fluoride is added into toothpaste so that certain anti-caries effect is achieved conveniently and quickly while cleaning teeth. However, toothpaste stays and acts only for a short period of time in oral cavity.

Fluoride foam, which is an internationally recognized quick and effective anti-caries technique. The anti-caries effect is achieved by applying highly concentrated fluoride foam on teeth and let it act for three minutes. At present, fluoride foam is substantially only used to prevent caries for preschoolers.

Fluoride varnish, which is a technique by applying varnish containing highly concentrated fluoride ions on tooth surface to prevent caries. Typical representatives of fluoride varnish are Duraphat of Colgate and White Varnish of 3M. It is required that fluoride varnish must be applied by a dental professional. At present, the technique is only performed clinically, and consumers cannot use fluoride varnish by themselves.

The Inventors of the present application believe that in view of the importance of caries prevention, it is necessary to provide different anti-caries means.

SUMMARY

In one aspect, the present application provides an anti-caries film, it contains a fluorine-containing silane, a film-forming agent, and an acidic substance.

In some embodiments, the weight content of fluorine in the anti-caries film is equal to or greater than 500 ppm.

In some embodiments, the weight content of fluorine in the anti-caries film is 500~11200 ppm.

In some embodiments, the acidic substance is weakly acidic antibacterial agent.

In some embodiments, the film-forming agent may be one of the following: aromatic isocyanate, acrylate, and a mixture thereof.

In another aspect, the present application provides an anti-caries solution for forming anti-caries film, the anti-caries solution contains a fluorine-containing silane, a film-forming agent, an acidic substance and an organic solvent.

In some embodiments, the weight content of the fluorine-containing silane is 0.1%~10%, the weight content of the film-forming agent is 5%~25%, the weight content of the acidic substance is 0.1%~1%, the weight content of the organic solvent is 75%~90%.

In some embodiments, the acidic substance is weakly acidic antibacterial agent.

In some embodiments, the film-forming agent may be one of the following: aromatic isocyanate, acrylate, and a mixture thereof.

In another aspect, the present application provides a dental appliance, which includes: a body having a surface facing teeth, and an anti-caries film which has a certain thickness, is formed on at least a partial area of the surface facing teeth, and is able to react with saliva to release fluoride ions, the anti-caries film contains a fluorine-containing silane, a film-forming agent, and an acidic sub stance.

In some embodiments, the thickness of the anti-caries film may be less than 50 μm.

In some embodiments, the dental appliance may be a shell-shaped dental appliance which forms a cavity for receiving teeth, the inner surface of the cavity is the surface facing teeth.

In some embodiments, the weight content of fluorine in the anti-caries film is equal to or greater than 500 ppm.

In some embodiments, the weight content of fluorine in the anti-caries film is 50011200 ppm.

In some embodiments, the acidic substance is weakly acidic antibacterial agent.

In some embodiments, the film-forming agent may be one of the following: aromatic isocyanate, acrylate, and a mixture thereof.

In another aspect, the present application provides a method for forming anti-caries film on dental appliance, the method includes: applying an anti-caries solution on at least partial area of a surface facing teeth of a dental appliance, and letting the anti-caries solution cure to form an anti-caries film, wherein the anti-caries solution contains a fluorine-containing silane, a film-forming agent, an acidic substance and an organic solvent.

In some embodiments, the weight content of the fluorine-containing silane is 0.1%~10%, the weight content of the film-forming agent is 5%~25%, the weight content of the acidic substance is 0.1%~1%, the weight content of the organic solvent is 75%~90%.

In some embodiments, the acidic substance is weakly acidic antibacterial agent.

In some embodiments, the film-forming agent may be one of the following: aromatic isocyanate, acrylate, and a mixture thereof.

In some embodiments, the dental appliance may be a shell-shaped dental appliance which forms a cavity for receiving teeth, the inner surface of the cavity is the surface facing teeth.

In some embodiments, the thickness of the anti-caries film may be less than 50 μm.

In some embodiments, the organic solvent volatilizes with the cure of the anti-caries solution, therefore the content of the organic solvent in the anti-caries film is almost zero.

BRIEF DESCRIPTION OF THE DRAWINGS

The above and other features of the present application will be further illustrated below with reference to figures and their detailed description. It should be appreciated that these figures only show several exemplary embodiments according to the present application, so they should not be construed as limiting the protection scope of the present application. Unless otherwise specified, the figures are not necessarily drawn to scale, and similar reference numbers therein denote similar components.

DETAILED DESCRIPTION OF ILLUSTRATED EMBODIMENTS

In the following detailed description, reference is made to the accompanying drawings, which form a part thereof. Exemplary embodiments in the detailed description and figures are only intended for illustration purpose and not meant to be limiting. Inspired by the present application, those skilled in the art can understand that other embodiments may be utilized and other changes may be made, without departing from the spirit or scope of the present application. It will be readily understood that aspects of the present application described and illustrated herein can be arranged, replaced, combined, separated and designed in a wide variety of different configurations, all of which are explicitly contemplated and make part of the present application.

Shell-shaped dental appliances such as shell-shaped tooth repositioners, retainers and snore stoppers made of polymer materials become more and more popular due to their advantages on aesthetic appearance, convenience and hygiene.

Usually, a shell-shaped dental appliance is worn for long hours daily. For shell-shaped tooth repositioner, a patient is required to wear it all day long except during eating and tooth brushing, generally, for no less than 22 hours daily. Furthermore, an orthodontic treatment might take up to 1-3 years. For shell-shaped retainer and snore stopper, a patient needs to wear it during sleep, and might need to use it in lifetime.

A shell-shaped dental appliance isolates teeth from the oral cavity environment for a long term, keeps the teeth in a relatively closed anoxic environment, and hinders the normal contact of saliva with the teeth (saliva is critical for oral hygiene, it washes away bacteria from the oral cavity and maintains microbial balance, and enzymes in saliva decompose food residues). Therefore, wearing a shell-shaped dental appliance can accelerate reproduction of anaerobic bacteria on surfaces of teeth, resulting in dental plaque, and then causing many problems such as caries, yellow teeth, periodontal disease and halitosis.

The Inventors of the present application realize the necessity of providing different anti-caries means on the one hand, and realize the above problems of shell-shaped dental appliance on the other hand. Motivated by this, the Inventors developed an anti-caries film, an anti-caries solution for forming anti-caries film, a method for forming anti-caries film and a dental appliance having anti-caries film thereon.

Inspired by the present application, it is readily understood that besides shell-shaped dental appliances mentioned above, anti-caries film may be formed on any other suitable dental appliance, especially on a surface that is in contact with teeth, to achieve anti-caries effect. A method for forming anti-caries film according to one embodiment of the present application is described in detail taking shell-shaped dental appliance as an example.

Figure 1:
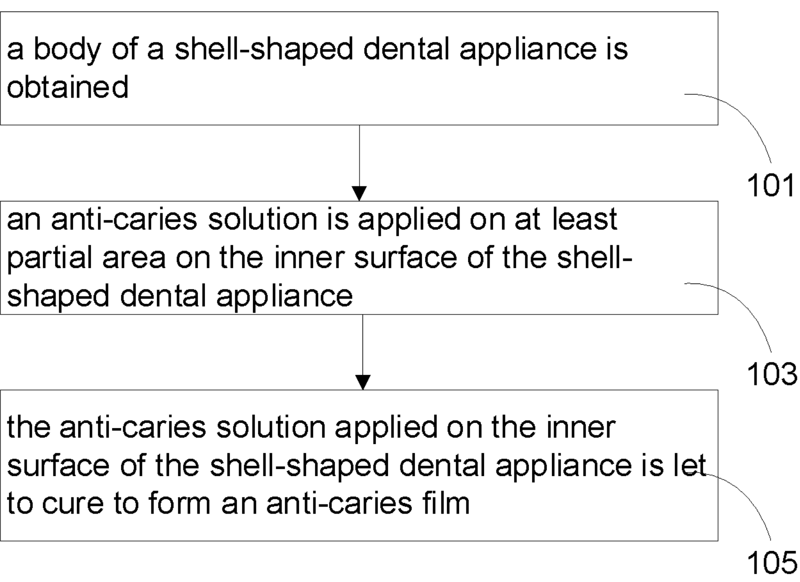
FIG. 1 schematically illustrates a flow chart of a method for fabricating a shell-shaped dental appliance according to one embodiment of the present application.

Referring to FIG. 1, it schematically illustrates a flow chart of a method 100 of forming anti-caries film according to one embodiment of the present application.

In 101, a body of a shell-shaped dental appliance is obtained.

The body of the shell-shaped dental appliance is made of a polymer material, which body is an integral shell and forms a cavity for receiving teeth, wherein the geometry of at least a part of the cavity substantially matches a corresponding part of a patient's tooth arrangement.

At present, the most commonly used method for fabricating a body of a shell-shaped dental appliance is thermoforming technique. The basic process of the method includes thermoforming a heated polymer sheet material on a teeth model, trimming and polishing the thermoformed negative model after cooling to obtain the body of the shell-shaped dental appliance.

In one embodiment, the body of the shell-shaped dental appliance may be constructed of a single layer of material. In another embodiment, the body of the shell-shaped dental appliance may be constructed of two or more layers of materials.

In one embodiment, the cavity of the body of the shell-shaped dental appliance is for receiving an entire dentition. In a further embodiment, the cavity of the body of the shell-shaped dental appliance is for receiving a part of a dentition only (a plurality of teeth).

In one embodiment, the shell-shaped dental appliance may be a shell-shaped orthodontic repositioner for repositioning a patient's teeth from a current first tooth arrangement to a second tooth arrangement. In this example, the model of teeth for fabricating the body of the shell-shaped dental appliance may substantially match the second tooth arrangement of the patient's teeth, or slightly deviate towards the repositioning direction so that the shell-shaped dental appliance is able to reposition the patient's teeth to the second tooth arrangement.

In a further embodiment, the body of the shell-shaped dental appliance may be fabricated using a 3D printing technology. In yet another embodiment, the body of the shell-shaped dental appliance may be fabricated by cutting a blank using a numerical control machine.

In 103, an anti-caries solution is applied on at least a partial area of an inner surface of the body of the shell-shaped dental appliance.

The inner surface of the shell-shaped dental appliance is a surface that faces teeth.

In one embodiment, the anti-caries solution may be applied only on an area that needs to be formed with anti-caries film. In another embodiment, the anti-caries solution may be applied on the whole inner surface of the shell-shaped dental appliance.

Inspired by the present application, it is readily understood that any suitable method may be used to apply the anti-caries solution, for example, brush, spray or dip etc.

In one embodiment, the anti-caries solution contains an organic solvent, a film-forming agent, a fluorine-containing substance and an acidic substance.

The organic solvent is used to dissolve the film-forming agent and the fluorine-containing substance and mix them uniformly. Examples of the organic solvent comprise but are not limited to: ethyl acetate, butyl acetate, isoamyl acetate, isoamyl propionate, isoamyl butyrate etc. and mixtures thereof. During the formation of the anti-caries film, the organic solvent in the anti-caries solution is gradually volatilized, and the anti-caries film almost does not contain the organic solvent. Therefore, while wearing the shell-shaped dental appliance of the present application, the patient will not feel uncomfortable because of the organic solvent.

The film-forming agent is a polymer capable of forming a continuous film, and its examples comprise but are not limited to aromatic isocyanate, acrylate, and a mixture thereof. It is understood that aromatic isocyanate and acrylate each refer to a class of substances, and may comprise different specific substances. Therefore, the film-forming agent may be a mixture of two or more types of aromatic isocyanate, a mixture of two or more types of acrylate, or a mixture of one or more types of aromatic isocyanate and one or more types of acrylate.

On the one hand, the aromatic isocyanate and acrylate film-forming agent is colorless and transparent, and is able to form a colorless and transparent film, which keeps the appearance of a shell-shaped dental appliance unchanged. In the case where the color of the shell-shaped dental appliance needs to be changed, a colorant may be mixed into the anti-caries solution, so that the part of the shell-shaped dental appliance covered with the anti-caries film exhibits a desired color. On the other hand, viscosities of aromatic isocyanate and acrylate film-forming agents are low, so that the anti-caries solution has good leveling performance and it is easy to apply it on a surface evenly.

Inspired by the present application, it is understood that the physical properties (e.g. hardness and adhesive property) of the anti-caries film mainly depend on the film-forming agent, and the film-forming agent may be selected according to specific conditions and needs.

The fluorine-containing substance is able to react with saliva to generate fluoride ions to achieve anti-caries effect. In one embodiment, the fluorine-containing substance may be a fluorine-containing organic compound that can be hydrolyzed to release fluoride ions. In one embodiment, the fluorine-containing substance may be a fluorine-containing organosilane whose structural formula is $R—[SiF_m(OH)_{3-m}]_n$, wherein m is in a range of 1~3, and n is in a range of 1~4.

The fluorine containing organosilane releases fluoride ions and silanol by hydrolysis. The inventors of the present application discovered that the rate of reaction of hydrolysis under neutral environment is relatively slow, if an acidic substance is added, it will ionize and release hydrogen ions, and this will catalyze the hydrolysis of the fluorine containing organosilane and accelerate the release of fluoride ions. Therefore, an acidic substance may be used to control the rate of the release of fluoride ions.

In one embodiment, a weakly acidic antibacterial agent may be used to accelerate the release of fluoride ions, and to achieve antibacterial effect at the same time. Examples of weakly acidic antibacterial agent include but are not limited to tea polyphenols, catechin, theaflavin, lemon oil, chlorhexidine, and cetylpyridinium chloride etc.

In one embodiment, contents of various components of the anti-caries solution may be as follows: the weight content of the fluorine containing substance is 0.1%~10%, the weight content of the film forming agent is 5%~25%, the weight content of the organic solvent is 75%~90%, the weight content of the acidic substance is 0.1%~1%.

In one embodiment, in order to better wearing experience, the anti-caries solution may further comprise an aromatic. Examples of the aromatic include but are not limited to: menthol, coolants, fruit flavoring essences etc.

In one embodiment, contents of various components of the anti-caries solution may be as follows: the weight content of the fluorine containing substance is 0.1%~10%, the weight content of the film forming agent is 5%~25%, the weight content of the organic solvent is 75%~90%, the weight content of the acidic substance is 0.1%~1%, the weight content of the aromatic is 0.05%~0.1%.

In 105, the anti-caries solution applied on the inner surface of the shell-shaped dental appliance is cured to form an anti-caries film.

In one embodiment, after the organic solvent in the anti-caries solution applied on the inner surface of the shell-shaped dental appliance volatizes, the rest substances will form an anti-caries film having certain thickness on the inner surface of the shell-shaped dental appliance.

In one embodiment, the weight content of fluoride in the anti-caries film is equal to or greater than 500 ppm. In another embodiment, the weight content of fluoride in the anti-caries film is 500~11200 ppm.

The anti-caries film is attached to the inner surface of the shell-shaped dental appliance body and has a certain thickness.

In one embodiment, the anti-caries film may be formed only on a selected area of the inner surface of the body of the shell-shaped dental appliance, and the area may be selected according to specific conditions and needs. In yet another embodiment, the anti-caries film may be formed on the entire inner surface of the body of the shell-shaped dental appliance.

In one embodiment, an anti-caries solution may be applied on the inner surface of the body of the shell-shaped dental appliance, and the anti-caries film is formed after the solution cures.

Figure 2:
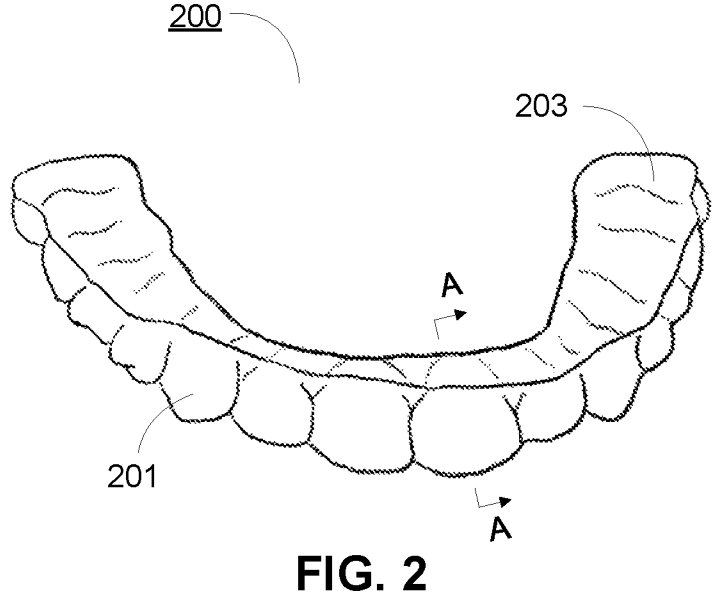
FIG. 2 schematically illustrates a shell-shaped dental appliance according to one embodiment of the present application.
Figure 3:
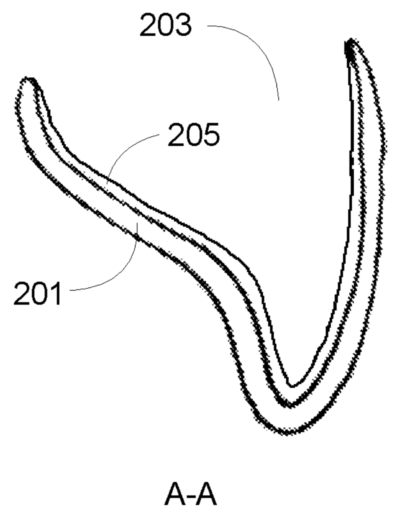
FIG. 3 schematically illustrates a cross-sectional view along line A-A of the shell-shaped dental appliance shown in FIG. 2.

Please refer to FIG. 2 and FIG. 3, wherein FIG. 2 schematically illustrates a shell-shaped dental appliance 200 according to one embodiment of the present application, and FIG. 3 schematically illustrates a cross-sectional view taken along the line A-A of the shell-shaped dental appliance 200 shown in FIG. 2.

The shell-shaped dental appliance 200 comprises a body 201 that is an integral shell and forms a cavity 203 for receiving teeth. An anti-caries film 205 is formed on the inner surface of the body 201 (i.e. the surface of the cavity 203).

In one embodiment, the thickness of the anti-caries film 205 may be determined depending on specific needs and conditions. For example, for a shell-shaped tooth repositioner fabricated using thermoforming technique, if tolerance of error of physical model of teeth is ±100 μm, the thickness of the anti-caries film 205 may be controlled to be below 50 μm (micrometer), or even below 25 μm, so that the anti-caries film 205 basically does not affect the orthodontic performance of the shell-shaped tooth repositioner.

The rates of release of fluoride of anti-caries films with and without acidic substance will compared below.

Example 1

The composition of the anti-caries solution is as follows:

a fluorine-containing organic compound (a fluorine-containing organic compound that is more soluble in organic solvent): 1% fluorine-containing organosilane with a fluorine content of about 0.1%;

a film-forming agent: 11% aromatic isocyanate film-forming agent;

an organic solvent: 62.9% ethyl acetate and 25% isoamyl propionate;

a weakly acidic antibacterial agent: 0.1% epigallocatechin gallate.

The anti-caries solution is evenly applied on the inner surface of the shell-shaped tooth repositioner with a brush and is let to cure at a room temperature.

Wherein, the structural formula of fluorine-containing organosilane is as follows:

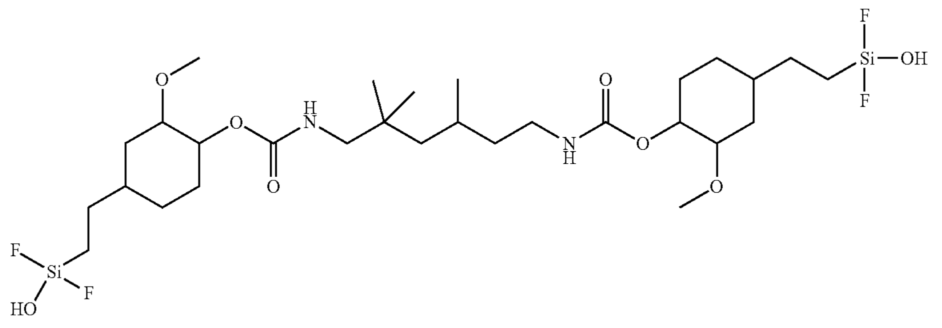 [SMILES: COC1CC(CC[Si](O)(F)F)CCC1OC(=O)NCCC(C)CC(C)(C)CNC(=O)OC1CCC(CC[Si](O)(F)F)CC1OC]

In this example, the film-forming agent is toluene diisocyanate-trimethylolpropane-diethylene glycol adduct, and it is cured by reacting with water vapor in the air.

In this example, the adhesion between the anti-caries film and the shell-shaped tooth repositioner is strong, and it reaches the highest grade ISO 2409:2013-2a-0 in a cross-cut test.

The pencil hardness level of the anti-caries film reaches H level.

Example 2

The composition of the anti-caries solution is as follows:

a fluorine-containing organic compound: 1% fluorine-containing organosilane with a fluorine content about 0.1% (same as Example 1);

a film-forming agent: 11% aromatic isocyanate;

an organic solvent: 63% ethyl acetate and 25% Isoamyl propionate.

The anti-caries solution is evenly applied on the inner surface of the shell-shaped tooth repositioner with a brush and is let to cure at a room temperature.

Please refer to below Table 1, it shows the rates of release of fluoride of the anti-caries films of Example 1 (contains acidic substance) and Example 2 (does not contain acidic substance).

TABLE 1

| soaking time | content of released fluoride (ppm) | | |
|---|---|---|---|
| (hour) | Example 2 | Example 1 | increase rate |
| 1 | 565 | 694 | 22.8% |
| 2 | 652 | 794 | 21.8% |
| 6 | 725 | 896 | 23.6% |

According to Table 1, the fluoride release rate of anti-caries film containing acidic substance is substantially higher than that of anti-caries film containing no acidic substance.

It is understood that as long as a sufficient amount of fluoride ions is released, a sufficient anti-caries effect can be achieved. The anti-caries effect of the anti-caries films of the above two examples last for 3 to 6 months.

While various aspects and embodiments have been disclosed herein, other aspects and embodiments will be apparent to those skilled in the art, inspired by the present application. The various aspects and embodiments disclosed herein are for illustration only and are not intended to be limiting, and the scope and spirit of the present application shall be defined by the following claims.

Likewise, the various diagrams may depict exemplary architectures or other configurations of the disclosed methods and systems, which are helpful for understanding the features and functions that can be included in the disclosed methods and systems. The claimed invention is not restricted to the illustrated exemplary architectures or configurations, and desired features can be achieved using a variety of alternative architectures and configurations. Additionally, with regard to flow diagrams, functional descriptions and method claims, the order in which the blocks are presented herein shall not mandate that various embodiments of the functions shall be implemented in the same order unless otherwise the context specifies.

Unless otherwise specifically specified, terms and phrases used herein are generally intended as “open” terms instead of limiting. In some embodiments, use of phrases such as “one or more”, “at least” and “but not limited to” should not be construed to imply that the parts of the present application that do not use similar phrases intend to be limiting.

We claim:

1. An anti-caries film on a dental appliance, wherein the anti-caries film is formed of an anti-caries solution containing a fluorine-containing silane, a film-forming agent, an acidic substance and an organic solvent; the organic solvent is a mixture of ethyl acetate and isoamyl propionate; the film-forming agent is toluene diisocyanate-trimethylolpropanediethylene glycol adduct, the acidic substance is epigallocatechin gallate, the fluorine-containing silane is a fluorine-containing organosilane whose structural formula is

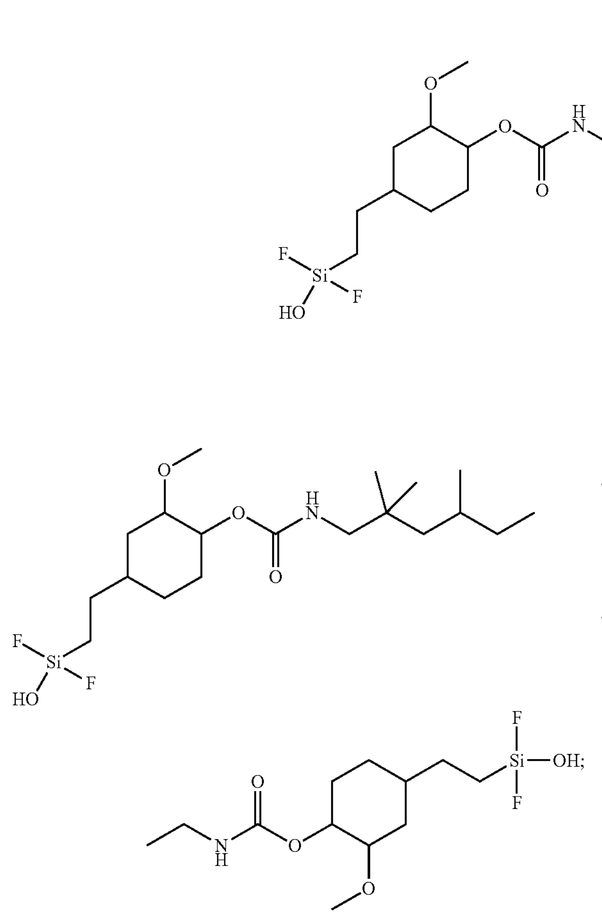

and wherein the weight content of the fluorine-containing silane is 0.1%~10%, the weight content of the film-forming agent is 5%~25%, the weight content of the acidic substance is 0.1%~1%, the weight content of the organic solvent is 75%~90%.

2. The anti-caries film of claim 1, wherein the weight content of fluorine in the anti-caries film is equal to or greater than 500 ppm.

3. The anti-caries film of claim 2, wherein the weight content of fluorine in the anti-caries film is 500~11200 ppm.

4. The anti-caries film of claim 1, wherein the weight content of the fluorine-containing silane is 1%, the weight content of the film-forming agent is 11%, the weight content of the acidic substance is 0.1%, the weight content of ethyl acetate is 62.9% and the weight content of isoamyl propionate is 25%.

5. An anti-caries solution for forming an anti-caries film on a dental appliance, containing: a fluorine-containing silane, a film-forming agent, an acidic substance and an organic solvent; the organic solvent is a mixture of ethyl acetate and isoamyl propionate; the film-forming agent is toluene diisocyanate-trimethylolpropanediethylene glycol adduct, the acidic substance is epigallocatechin gallate, the fluorine-containing silane is a fluorine-containing organosilane whose structural formula is and wherein the weight content of the fluorine-containing silane is 0.1%~10%, the weight content of the film-forming agent is 5%~25%, the weight content of the acidic substance is 0.1%~1%, the weight content of the organic solvent is 75%~90%.

6. The anti-caries solution of claim 5, wherein the weight content of the fluorine-containing silane is 1%, the weight content of the film-forming agent is 11%, the weight content of the acidic substance is 0.1%, the weight content of ethyl acetate is 62.9% and the weight content of isoamyl propionate is 25%.

7. A dental appliance, comprising:

a body having a surface facing teeth, and an anti-caries film which has a certain thickness, is formed on at least a partial area of the surface facing teeth, and is able to react with saliva to release fluoride ions, wherein the anti-caries film is formed of an anti-caries solution containing a fluorine-containing silane, a film-forming agent, an acidic substance and an organic solvent; the organic solvent is a mixture of ethyl acetate and isoamyl propionate; the film-forming agent is toluene diisocyanate-trimethylolpropanediethylene glycol adduct, the acidic substance is epigallocatechin gallate, the fluorine-containing silane is a fluorine-containing organosilane whose structural formula is

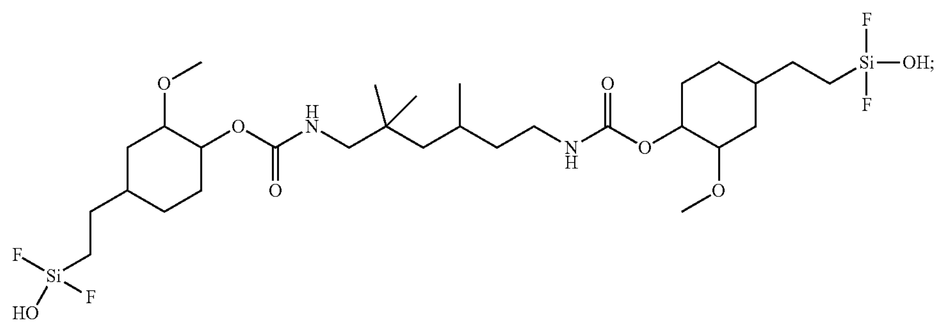 [SMILES: COC1CC(CC[Si](O)(F)F)CCC1OC(=O)NCCC(C)CC(C)(C)CNC(=O)OC1CCC(CC[Si](O)(F)F)CC1OC]

and wherein the weight content of the fluorine-containing silane is 0.1%~10%, the weight content of the film-forming agent is 5%~25%, the weight content of the acidic substance is 0.1%~1%, the weight content of the organic solvent is 75%~90%.

8. The dental appliance of claim 7, wherein the thickness of the anti-caries film is less than 50 μm.

9. The dental appliance of claim 7, wherein the dental appliance is a shell-shaped dental appliance which forms a cavity for receiving teeth, the inner surface of the cavity is the surface facing teeth.

letting the anti-caries solution cure to form an anti-caries film, wherein the anti-caries solution contains a fluorine-containing silane, a film-forming agent, an acidic substance and an organic solvent;

wherein the organic solvent is a mixture of ethyl acetate and isoamyl propionate; the film-forming agent is toluene diisocyanate-trimethylolpropanediethylene glycol adduct, the acidic substance is epigallocatechin gallate, the fluorine-containing silane is a fluorine-containing organosilane whose structural formula is

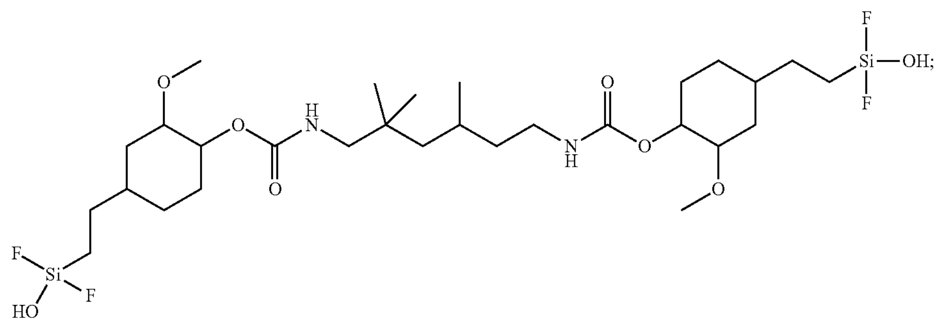 [SMILES: COC1CC(CC[Si](O)(F)F)CCC1OC(=O)NCCC(C)CC(C)(C)CNC(=O)OC1CCC(CC[Si](O)(F)F)CC1OC]

10. The dental appliance of claim 7, wherein the weight content of fluorine in the anti-caries film is equal to or greater than 500 ppm.

11. The dental appliance of claim 10, wherein the weight content of fluorine in the anti-caries film is 500~11200 ppm.

12. The dental appliance of claim 7, wherein the weight content of the fluorine-containing silane is 1%, the weight content of the film-forming agent is 11%, the weight content of the acidic substance is 0.1%, the weight content of ethyl acetate is 62.9% and the weight content of isoamyl propionate is 25%.

13. A method for forming an anti-caries film on a dental appliance, comprising:

applying an anti-caries solution on at least partial area of a surface facing teeth of a dental appliance, and and wherein the weight content of the fluorine-containing silane is 0.1%~10%, the weight content of the film-forming agent is 5%~25%, the weight content of the acidic substance is 0.1%~1%, the weight content of the organic solvent is 75%~90%.

14. The method of claim 13, wherein the applying of the anti-caries solution is controlled so that the thickness of the anti-caries film is less than 50 μm.

15. The method of claim 13, wherein the organic solvent volatilizes with the cure of the anti-caries solution, therefore the content of the organic solvent in the anti-caries film is almost zero.

16. The method of claim 13, wherein the weight content of the fluorine-containing silane is 1%, the weight content of the film-forming agent is 11%, the weight content of the acidic substance is 0.1%, the weight content of ethyl acetate is 62.9% and the weight content of isoamyl propionate is 25%.

* * * * *